United States Patent
Inaba et al.

(10) Patent No.: US 6,476,232 B2
(45) Date of Patent: Nov. 5, 2002

(54) 4-(2-AMINO-1-HYDROXYETHYL) OXAZOLINE DERIVATIVE AND METHOD FOR PRODUCING SAME

(75) Inventors: Takashi Inaba; Yasuki Yamada, both of Takatsuki (JP)

(73) Assignees: Japan Tobacco Inc., Tokyo (JP); Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/983,978

(22) Filed: Oct. 26, 2001

(65) Prior Publication Data

US 2002/0049337 A1 Apr. 25, 2002

Related U.S. Application Data

(62) Division of application No. 09/835,487, filed on Apr. 17, 2001, which is a division of application No. 09/580,831, filed on May 30, 2000, now Pat. No. 6,252,085, which is a division of application No. 09/043,668, filed on Apr. 14, 1998, now Pat. No. 6,133,461.

(30) Foreign Application Priority Data

Sep. 26, 1995 (JP) .............................................. 7-248183

(51) Int. Cl.[7] ...................... C07D 413/00; C07D 215/00
(52) U.S. Cl. ........................ 548/237; 548/239; 546/164
(58) Field of Search ................................ 548/237, 239; 546/164

(56) References Cited

FOREIGN PATENT DOCUMENTS

| JP | 56-127373 | 10/1981 |
|---|---|---|
| JP | 6-271534 | 9/1994 |
| WO | 95/09843 | 4/1995 |

OTHER PUBLICATIONS

Journal of Organic Chemistry, vol. 58, No. 23, 1993, pp. 6180–6181.

*Primary Examiner*—Amelia Owens
(74) *Attorney, Agent, or Firm*—Wenderoth, Lind & Ponack, L.L.P.

(57) ABSTRACT

A 4-(2-amino-1-hydroxyethyl)oxazoline derivative of the formula [XIII]

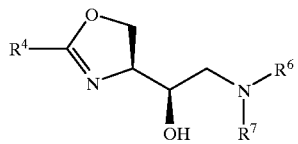

[XIII]

and a method for producing the same, in which $R^4$ is an optionally substituted alkyl, an optionally substituted aryl, an optionally substituted heteroaryl, an optionally substituted aralkyl or an optionally substituted heteroarylalkyl, and $R^6$ and $R^7$ are the same or different and each is a hydrogen atom, an optionally substituted alkyl, an optionally substituted aryl, an optionally substituted heteroaryl or an optionally substituted aralkyl, or $R^6$ and $R^7$ combinedly form, together with the adjacent nitrogen atom, a hetero ring, the hetero ring being optionally substituted by halogen atom, alkyl, alkenyl, alkoxy, amino, alkoxycarbonyl, carboxamide or alkyl-substituted carbamoyl, an enantiomer thereof or a salt thereof.

3 Claims, No Drawings

4-(2-AMINO-1-HYDROXYETHYL) OXAZOLINE DERIVATIVE AND METHOD FOR PRODUCING SAME

This application is a divisional of Ser. No. 09/835,487 filed Apr. 17, 2001, which is a divisional of Ser. No. 09/580,831 filed May 30, 2000, now U.S. Pat. No. 6,252,085, which is a divisional of Ser. No. 09/043,668 filed Apr. 14, 1998, now issued as U.S. Pat. No. 6,133,461.

TECHNICAL FIELD

The present invention relates to a novel method for producing a compound of the formula [XVI]

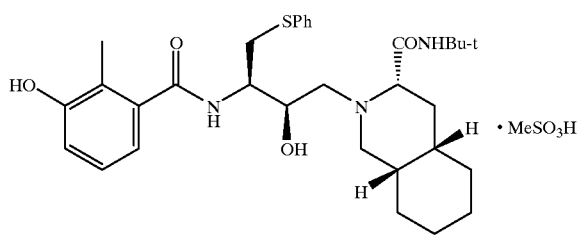

[XVI]

wherein Me is methyl, Bu-t is t-butyl and Ph is phenyl, which is useful as a treatment drug of HIV-related diseases based on its inhibitory action on proteases derived from viruses, various novel intermediates useful for producing said compound [XVI], and to the method for production of the intermediates. These intermediates can be used for not only production of the above-mentioned compound [XVI] but also for production of various compounds.

BACKGROUND ART

The above-mentioned compound [XVI] useful as an HIV protease inhibitor is known as described in WO95/09843. This compound [XVI] has been conventionally produced from serine as a starting material, by increasing carbon and numerous other steps inclusive of stereoselective reduction of carbonyl group. Such conventional production method is extremely complicated and inefficient, since it requires expensive starting materials and constant low temperature conditions for reactions. Accordingly, there remain many problems to be solved before the conventional synthetic method is actually put to industrial practice.

In addition, 2,2-dimethyl-6-amino-1,3-dioxepan-5-ol which is described, for example, in U.S. Pat. No. 4,439,613 is an intermediate for producing a compound useful as an X ray contrast medium, and even though the compound obtained is a racemate, resolution of the racemate itself by a method such as recrystallization has been extremely difficult. Moreover, this U.S. patent does not suggest production of specific enantiomers of the present invention.

Accordingly, an object of the present invention is to provide a method for stereoselectively and extremely efficiently producing the above-mentioned compound [XVI] useful as an HIV protease inhibitor upon solution of the above-mentioned problems. Another object of the present invention is to provide a novel intermediate useful for producing said compound and a production method thereof.

DISCLOSURE OF THE INVENTION

The present inventors have made intensive studies in an attempt to achieve the above-mentioned objects, and found that a step comprising acetalating or ketalating (z)-2-butene-1,4-diol, and epoxidation of the obtained compound to give a 3,5,8-trioxabicyclo[5.1.0]octane derivative, which is followed by an epoxy ring-opening reaction using a chiral amine, leads to a stereospecific (5R,6S)-6-substituted amino-1,3-dioxepan-5-ol derivative or an enantiomer thereof, from which a compound of the following formula [XV], that is, a compound inclusive of the aforementioned compound [XVI] useful as an HIV protease inhibitor, can be extremely efficiently produced stereoselectively through various other steps, which resulted in the completion of the present invention.

Thus, the present invention provides the following (1) to (15).

(1) A (5R,6S)-6-substituted amino-1,3-dioxepan-5-ol derivative of the formula [V]

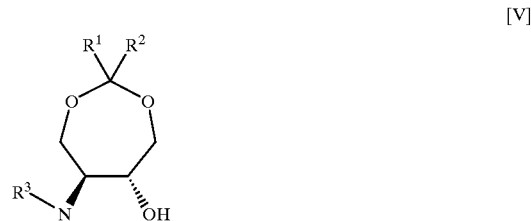

[V]

wherein $R^1$ and $R^2$ are the same or different and each is a hydrogen atom, an alkyl or an aryl, or $R^1$ and $R^2$ combinedly form a cycloalkyl ring together with the adjacent carbon atom, and $R^3$ is an aralkylamine residue or amino acid derivative residue having an (R) or (S) configuration, an enantiomer thereof and a salt thereof.

(2) A method for producing a (5R,6S)-6-substituted amino-1,3-dioxepan-5-ol derivative of the formula [V]

[V]

wherein $R^1$, $R^2$ and $R^3$ are as defined above, and an enantiomer thereof, comprising subjecting a 3,5,8-trioxabicyclo[5.1.0]octane derivative of the formula [III]

[III]

wherein $R^1$ and $R^2$ are as defined above, to an epoxy ring-opening reaction using a chiral amine of the formula [IV]

$R^3$—$NH_2$     [IV]

wherein $R^3$ is as defined above, and crystallizing a produced mixture of isomers.

(3) A (5R,6S)-6-amino-1,3-dioxepan-5-ol derivative of the formula [VI]

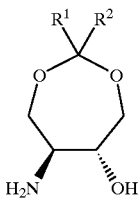

[VI]

wherein $R^1$ and $R^2$ are as defined above, an enantiomer thereof and a salt thereof.

(4) A method for producing a (5R,6S)-6-amino-1,3-dioxepan-5-ol derivative of the formula [VI]

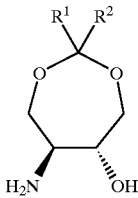

[VI]

wherein $R^1$ and $R^2$ are as defined above, an enantiomer thereof and a salt thereof, comprising subjecting a 3,5,8-trioxabicyclo[5.1.0]octane derivative of the formula [III]

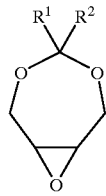

[III]

wherein $R^1$ and $R^2$ are as defined above, to an epoxy ring-opening reaction using a chiral amine of the formula [IV]

[IV]

wherein $R^3$ is as defined above, and crystallizing a produced mixture of isomers to give a (5R,6S)-6-substituted amino-1,3-dioxepan-5-ol derivative of the formula [V]

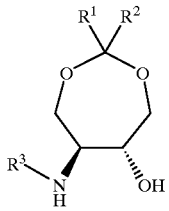

[V]

wherein $R^1$, $R^2$ and $R^3$ are as defined above, or an enantiomer thereof, and removing a substituent on an amino group of this compound to make the 6-position thereof a non-substituted amino group.

(5) An oxazoline derivative of the formula [X]

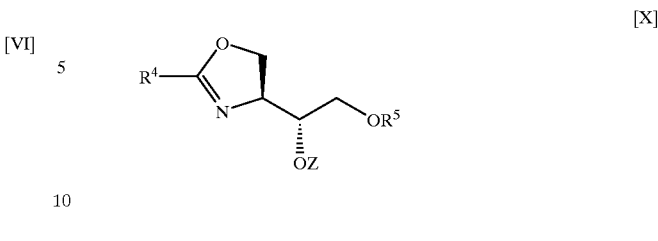

[X]

wherein $R^4$ is an optionally substituted alkyl, an optionally substituted aryl, an optionally substituted heteroaryl, an optionally substituted aralkyl or an optionally substituted heteroarylalkyl, $R^5$ is a hydrogen atom or an acyl, and Z is a substituent which functions as a leaving group together with an oxygen atom, an enantiomer thereof and a salt thereof.

(6) A method for producing an oxazoline derivative of the formula [X]

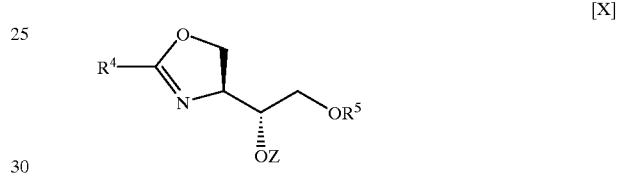

[X]

wherein $R^4$, $R^5$ and Z are as defined above, and an enantiomer thereof, comprising treating a 1,3-dioxepane derivative of the formula [IX]

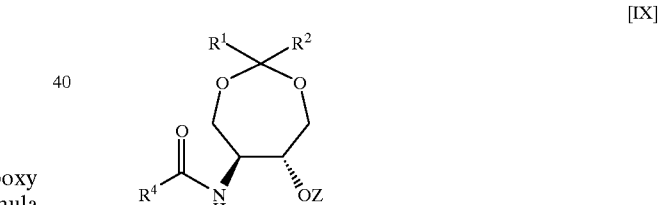

[IX]

wherein $R^1$, $R^2$, $R^4$ and Z are as defined above, or an enantiomer thereof, with a Lewis acid to form an oxazoline ring, followed by acylation as necessary.

(7) A method for producing an oxazoline derivative of the formula [X]

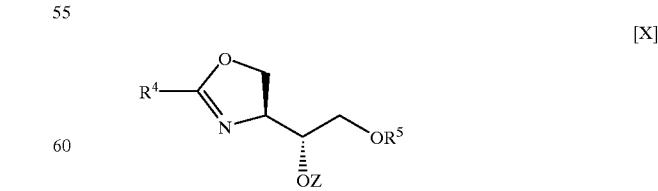

[X]

wherein $R^4$, $R^5$ and Z are as defined above, and an enantiomer thereof, comprising reacting a (5R, 6S)-6-amino-1,3-dioxepan-5-ol derivative of the formula [VI]

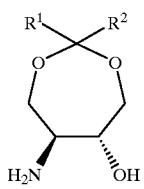

wherein R¹ and R² are as defined above, an enantiomer thereof or a salt thereof, with a reactive carboxylic acid derivative having R⁴ wherein R⁴ is as defined above, in the presence of a base, to give a (5R, 6S)-6-acylamino-1,3-dioxepan-5-ol derivative of the formula [VIII]

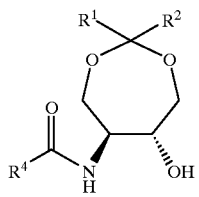

wherein R¹, R² and R⁴ are as defined above, or an enantiomer thereof, reacting the resulting compound with a sulfonylating agent, treating the resulting compound with a Lewis acid, and acylating said compound, where necessary.

(8) An (oxazolin-4-yl)oxirane derivative of the formula [XI]

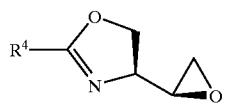

wherein R⁴ is as defined above, an enantiomer thereof and a salt thereof.

(9) A method for producing an (oxazolin-4-yl)oxirane derivative of the formula [XI]

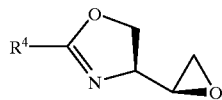

wherein R⁴ is as defined above, and an enantiomer thereof, comprising treating, with a base, an oxazoline derivative of the formula [X]

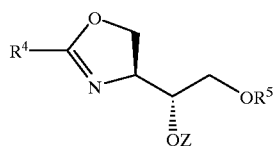

wherein R⁴, R⁵ and Z are as defined above, or an enantiomer thereof.

(10) A method for producing an (oxazolin-4-yl)oxirane derivative of the formula [XI]

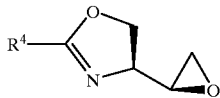

wherein R⁴ is as defined above, and an enantiomer thereof, comprising reacting a (5R,6S)-6-amino-1,3-dioxepan-5-olderivative of the formula [VI]

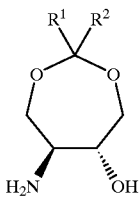

wherein R¹ and R² are as defined above, an enantiomer thereof or a salt thereof, with a reactive carboxylic acid derivative having R⁴ wherein R⁴ is as defined above, in the presence of a base, to give a (5R,6S)-6-acylamino-1,3-dioxepan-5-ol derivative of the formula [VIII]

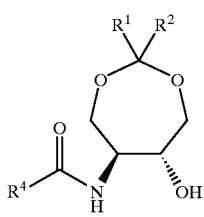

wherein R¹, R² and R⁴ are as defined above, or an enantiomer thereof, reacting the resulting compound with a sulfonylating agent, treating the resulting compound with a Lewis acid, and acylating said compound, where necessary, to give an oxazoline derivative of the formula [X]

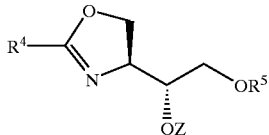

wherein R⁴, R⁵ and Z are as defined above, or an enantiomer thereof, and treating the obtained compound with a base.

(11) A 4-(2-amino-1-hydroxyethyl)oxazoline derivative of the formula [XIII]

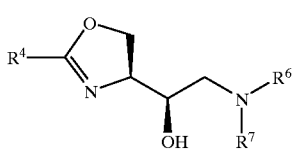

wherein R⁴ is as defined above, and R⁶ and R⁷ are the same or different and each is a hydrogen atom, an optionally substituted alkyl, an optionally substituted aryl, an optionally substituted heteroaryl or an optionally substituted aralkyl, or $R^6$ and $R^7$ combinedly form, together with the adjacent nitrogen atom, a hetero ring, said hetero ring being optionally substituted by halogen atom, alkyl, alkenyl, alkoxy, amino, alkoxycarbonyl, carboxamide or alkyl-substituted carbamoyl, an enantiomer thereof and a salt thereof.

(12) A method for producing a 4-(2-amino-1-hydroxyethyl) oxazoline derivative of the formula [XIII]

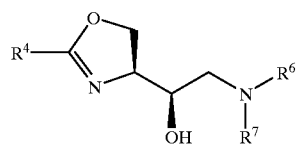

[XIII]

wherein $R^4$, $R^6$ and $R^7$ are as defined above, and an enantiomer thereof, comprising reacting an (oxazolin-4-yl) oxyrane derivative of the formula [XI]

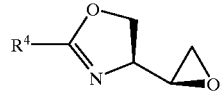

[XI]

wherein $R^4$ is as defined above, or an enantiomer thereof, with an amine of the formula [XII]

[XII]

wherein $R^6$ and $R^7$ are as defined above.

(13) A method for producing a 4-(2-amino-1-hydroxyethyl) oxazoline derivative of the formula [XIII]

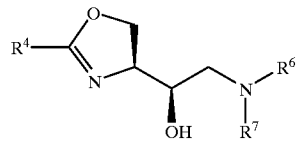

[XIII]

wherein $R^4$, $R^6$ and $R^7$ are as defined above, and an enantiomer thereof, comprising treating an oxazoline derivative of the formula [X]

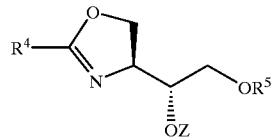

[X]

wherein $R^4$, $R^5$ and Z are as defined above, or an enantiomer thereof with a base to give an (oxazolin-4-yl)oxyrane derivative of the formula [XI]

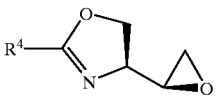

[XI]

wherein $R^4$ is as defined above, or an enantiomer thereof, and reacting the resulting derivative [XI] with an amine of the formula [XII]

[XII]

wherein $R^6$ and $R^7$ are as defined above.

(14) A method for producing an amide derivative of the formula [XV]

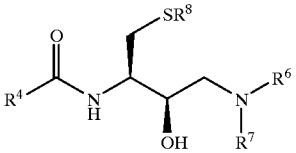

[XV]

wherein $R^4$, $R^6$ and $R^7$ are as defined above, and $R^8$ is a hydrogen atom, an alkyl, an optionally substituted aryl or an optionally substituted aralkyl, and an enantiomer thereof, comprising subjecting a 4-(2-amino-1-hydroxyethyl) oxazoline derivative of the formula [XIII]

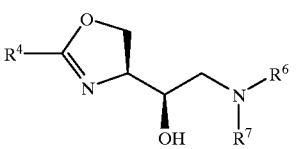

[XIII]

wherein $R^4$, $R^6$ and $R^7$ are as defined above, or an enantiomer thereof to ring opening with a mercaptane of the formula [XIV]

$R^8$—SH  [XIV]

wherein $R^8$ is as defined above.

(15) A method for producing an amide derivative of the formula [XV]

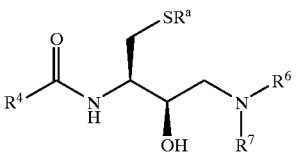

[XV]

wherein $R^4$, $R^6$, $R^7$ and $R^8$ are as defined above, and an enantiomer thereof, comprising reacting an (oxazolin-4-yl) oxirane derivative of the formula [XI]

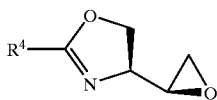

wherein R⁴ is as defined above, or an enantiomer thereof, with an amine of the formula [XII]

wherein R⁶ and R⁷ are as defined above, to give a 4-(2-amino-1-hydroxyethyl)oxazoline derivative of the formula [XIII]

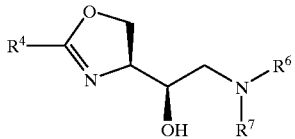

wherein R⁴, R⁶ and R⁷ are as defined above, or an enantiomer thereof, and subjecting this compound to ring opening with a mercaptane of the formula [XIV]

wherein R⁸ is as defined above.

As used herein, alkyl may be linear or branched and preferably has 1 to 6 carbon atom(s). Specific examples thereof include methyl, ethyl, propyl, isopropyl, butyl, isobutyl, s-butyl, t-butyl, pentyl, isopentyl, neopentyl, t-pentyl, hexyl, isohexyl, neohexyl, and the like. More preferred are lower alkyl having 1 to 4 carbon atom(s) such as methyl, ethyl, propyl, isopropyl, butyl, isobutyl, s-butyl and t-butyl.

The optionally substituted alkyl includes, for example, the above-mentioned alkyl which may be substituted by one or more substituent(s) which do(es) not influence the reaction. Examples of the substituents include hydroxy; halogen atoms such as fluorine, chlorine, bromine and iodine; amino; nitro; mono- or dialkylamino having 1 to 6 carbon atom(s) such as methylamino, ethylamino, hexylamino, dimethylamino and diethylamino; cyano; cycloalkyl having 3 to 7 carbon atoms such as cyclopropyl, cyclobutyl, cyclopentyl, cyclohexyl and cycloheptyl; alkoxy having 1 to 6 carbon atom(s) such as methoxy, ethoxy, propoxy, butoxy, pentyloxy and hexyloxy; carboxyl; alkoxycarbonyl having 2 to 6 carbon atoms such as methoxycarbonyl, ethoxycarbonyl, propoxycarbonyl, butoxycarbonyl and pentyloxycarbonyl; and the like. Preferred are hydroxy, halogen atom and amino.

The position and number of substituents on alkyl are not particularly limited.

The cycloalkyl ring formed by R¹ and R² in combination together with the adjacent carbon atom is preferably cycloalkyl ring having 3 to 7 carbon atoms, which is exemplified by cyclopropyl ring, cyclobutyl ring, cyclopentyl ring, cyclohexyl ring, cycloheptyl ring, and the like. Preferred is that having 4 to 6 carbon atoms, such as cyclobutyl ring, cyclopentyl ring and cyclohexyl ring.

The chiral amine is that having an asymmetric carbon atom adjacent to amino group, that is, amine having an (R) or (S) configuration. Typical examples include aralkylamine, amino acid derivative and the like.

Examples of aralkylamine include (R)-1-phenylethylamine, (S)-1-phenylethylamine, (R)-1-(1-naphthyl)ethylamine, (S)-1-(1-naphthyl)-ethylamine, (R)-α-phenylglycinol, (S)-α-phenylglycinol, and the like. Preferred is (R)-1-phenylethylamine.

The amino acid derivative includes, for example, amino acids having an asymmetric carbon atom adjacent to amino group, and derivatives thereof. Specific examples include amino acids such as (R)-serine, (S)-serine, (R)-α-phenylglycine and (S)-α-phenylglycine; amino acid derivatives such as (R)-serine methyl ester, (S)-serine methyl ester, (R)-α-phenylglycine methyl ester and (S)-α-phenylglycine methyl ester; and the like. Preferred is (R)-α-phenylglycine.

Aralkylamine residue and amino acid derivative residue respectively mean a group which is other than amino group and which binds to amino group in the above-mentioned aralkylamine and amino acid derivative.

Examples of aryl include phenyl, naphthyl, biphenyl, and the like. Preferred is phenyl.

The optionally substituted aryl includes, for example, the above-mentioned aryl which may be substituted by one or more substituent(s) having no influence on the reaction. Examples of the substituent include those exemplified with respect to the above-mentioned optionally substituted alkyl; alkyl having 1 to 6 carbon atom(s) such as methyl, ethyl, propyl, butyl, pentyl and hexyl; alkenyl having 2 to 6 carbon atoms such as vinyl, allyl, butenyl, pentenyl and hexenyl; acyloxy having 2 to 6 carbon atoms such as acetyloxy, propionyloxy, butyryloxy, pivaloyloxy and hexanoyloxy; and the like. Preferred are alkyl, hydroxy, halogen atom, amino, nitro, alkoxy and acyloxy, and more preferred are alkyl, hydroxy, halogen atom, alkoxy and acyloxy.

While the position and number of substituents on aryl are not particularly limited, preferred are compounds having 1 to 3 substituent(s) and more preferred are compounds having 1 or 2 substituent (s).

The aryl moiety of aralkyl is exemplified by those mentioned above such as phenyl, naphthyl and biphenyl, and the alkyl moiety thereof is exemplified by those mentioned above having 1 to 6 carbon atom(s). The aralkyl is exemplified by benzyl, phenethyl, phenylpropyl, phenylbutyl, phenylhexyl, and the like. Preferred is aralkyl comprising phenyl with C₁–C₄ alkyl.

The optionally substituted aralkyl is that which may be substituted by one or more substituent(s) which exert(s) no influence on the reaction. Examples of the substituent include those exemplified with respect to the aforementioned optionally substituted aryl; haloalkyl having 1 to 6 carbon atom(s) such as chloromethyl, chloroethyl and chlorobutyl; and the like. Preferred are hydroxy, halogen atom, alkyl, alkoxy, haloalkyl, nitro, acyloxy, amino and cyano. More preferred are halogen atom, alkyl, alkoxy and acyloxy. Specific examples of optionally substituted aralkyl include benzyl, halogen-substituted benzyl, alkyl-substituted benzyl, alkoxy-substituted benzyl, phenethyl, halogen-substituted phenethyl, alkyl-substituted phenethyl, alkoxy-substituted phenethyl, phenylpropyl, halogen-substituted phenylpropyl, alkyl-substituted phenylpropyl, alkoxy-substituted phenylpropyl, and the like. Preferred are benzyl, phenethyl, and the like.

While the position and number of substituents on aryl of the above-mentioned aralkyl are not particularly limited, preferred are compounds having 1 to 3 substituent(s).

Heteroaryl is, for example, pyridyl, pyrimidyl, pyrazinyl, furyl, thienyl, pyrrolyl, imidazolyl, oxazolyl, isoxazolyl, thiazolyl, isothiazolyl, indolyl, isoindolyl, quinolyl, isoquinolyl, phthalazinyl, naphthyridinyl, quinazolinyl, cinnolinyl or quinoxalinyl, with preference given to quinolyl and isoquinolyl.

The optionally substituted heteroaryl is that which may be substituted by one or more substituent(s) which exert(s) no influence on the reaction. Examples of the substituent include those exemplified with respect to the aforementioned optionally substituted aryl, and the like. Preferred are alkyl, hydroxy, halogen atom, amino, nitro, mono- or dialkylamino, alkoxy, acyloxy, carboxyl and alkoxycarbonyl. More preferred are alkyl, hydroxy, halogen atom, mono- or dialkylamino, alkoxy and acyloxy.

While the position and number of substituents on heteroaryl are not particularly limited, preferred are compounds having 1 to 3 substituent(s), and more preferred are compounds having 1 or 2 substituent(s).

The heteroaryl moiety of the heteroarylalkyl includes, for example, those exemplified above and the alkyl moiety includes, for example, those exemplified above having 1 to 6 carbon atom(s). Specific examples include 2-thienylmethyl, 3-furylmethyl, 4-pyridylmethyl, 2-quinolylmethyl, 3-isoquinolylmethyl, and the like. Preferred is 2-quinolylmethyl.

The optionally substituted heteroarylalkyl is, for example, that which may be substituted by one or more substituent(s) which exert(s) no influence on the reaction. Examples of the substituent include those exemplified with respect to the aforementioned optionally substituted heteroaryl, and the like.

While the position and number of substituents on heteroaryl of the above-mentioned heteroarylalkyl are not particularly limited, preferred are compounds having 1 to 3 substituent(s).

Examples of acyl include saturated aliphatic acyl preferably having 1 to 18 carbon atom(s), such as formyl, acetyl, propionyl, butyryl, isobutyryl, valeryl, isovaleryl, pivaloyl, hexanoyl, lauroyl, myristoyl, palmitoyl and stearoyl; unsaturated aliphatic acyl preferably having 3 to 18 carbon atoms, such as acryloyl, propioloyl, methacryloyl, crotonoyl and oleoyl; aromatic acyl, such as benzoyl, naphthoyl, toluoyl, hydratropoyl, atropoyl and cinnamoyl; heterocyclic acyl, such as furoyl, thenoyl, nicotinoyl and isonicotinoyl; acyl of hydroxy acid or alkoxylic acid, such as glycoloyl, lactoyl, glyceroyl, tropoyl, benziloyl, salicyloyl, anisoyl, vanilloyl, veratroyl, piperonyloyl, protocatechuoyl and galloyl; and the like. Preferred is saturated aliphatic acyl and more preferred are formyl, acetyl, propionyl and butyryl.

The hetero ring to be formed by $R^6$ and $R^7$ together with the adjacent nitrogen atom is, for example, saturated or unsaturated heteroaryl having one or more nitrogen atom(s). Specific examples include imidazolyl, triazolyl, tetrazolyl, pyrrolyl, pyrrolidinyl, imidazolidinyl, hydropyridyl, piperidino, piperazinyl, oxazinyl, morpholino, azepinyl, hydroazepinyl, indolyl, hydroindolyl, isoindolyl, hydroisoindolyl, hydroquinolyl, hydroisoquinolyl, and the like. Preferred are the groups represented by the following formulas

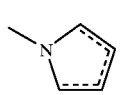 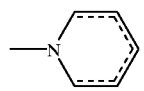 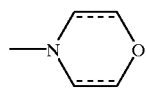

-continued

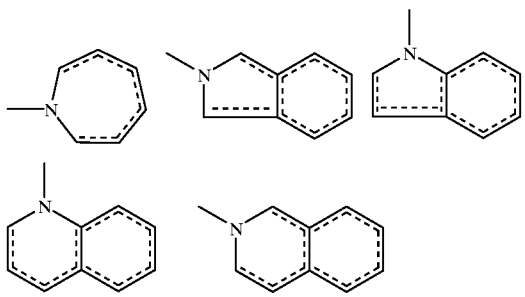

wherein the broken line may be either double bond or single bond, and more preferred is the group represented by the following formula:

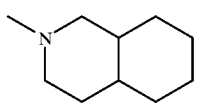

Said hetero ring may be substituted by halogen atom, alkyl having 1 to 6 carbon atom(s), alkenyl having 2 to 6 carbon atoms, alkoxy having 1 to 6 carbon atom(s), amino, alkoxycarbonyl having 2 to 6 carbon atoms, carboxamide, or alkyl-substituted carbamoyl wherein the alkyl moiety has 1 to 6 carbon atom(s).

While the position and number of substituents on hetero ring are not particularly limited, preferred are compounds having 1 to 3, more preferably 1 or 2, substituent(s).

The halogen atom as the substituent for hetero ring includes, for example, fluorine, chlorine, bromine and iodine.

The alkyl as the substituent for hetero ring includes, for example, the aforementioned ones having 1 to 6 carbon atom(s).

The alkenyl as the substituent for hetero ring includes, for example, linear or branched alkenyl preferably having 2 to 6 carbon atoms, which is exemplified by vinyl, allyl, crotyl, 2-pentenyl, 3-pentenyl, 2-hexenyl and 3-hexenyl. More preferred are those having 2 to 4 carbon atoms such as vinyl, allyl and crotyl.

The alkoxy as the substituent for hetero ring includes, for example, linear or branched alkoxy preferably having 1 to 6 carbon atom(s), which is exemplified by methoxy, ethoxy, propoxy, isopropoxy, butoxy, isobutoxy, s-butoxy, t-butoxy, pentyloxy, isopentyloxy, neopentyloxy, hexyloxy, and the like. More preferred are those having 1 to 4 carbon atom(s) such as methoxy, ethoxy, propoxy, isopropoxy and butoxy, with further preference given to those having 1 or 2 carbon atom(s) such as methoxy and ethoxy.

The alkoxycarbonyl as the substituent for hetero ring includes, for example, alkoxycarbonyl preferably having 2 to 6 carbon atoms, which is exemplified by the above-mentioned alkoxy having 1 to 5 carbon atom(s) with carbonyl group, and the like.

The alkyl-substituted carbamoyl as the substituent for hetero ring includes, for example, those wherein the alkyl moiety preferably has 1 to 6 carbon atom(s), which is exemplified by N-methylcarbamoyl, N-ethylcarbamoyl, N-propylcarbamoyl, N-t-butylcarbamoyl, N-pentylcarbamoyl, N-hexylcarbamoyl, and the like. Preferred is N-t-butylcarbamoyl.

The substituent (Z group) which functions as a leaving group together with oxygen atom includes, for example, as a group joining with oxygen atom (leaving group: OZ group), sulfonic acid derivatives such as tosyloxy (p-toluenesulfonyloxy), brosyloxy (p-bromobenzenesulfonyloxy), mesyloxy (methanesulfonyloxy), benzenesulfonyloxy, camphorsulfonyloxy and trifyloxy (trifluoromethanesulfonyloxy). Preferred is mesyloxy (methanesulfonyloxy).

The reactive carboxylic acid derivative having $R^4$ includes, for example, acid halides (e.g., $R^4COCl$ and $R^4COBr$), acid anhydrides (e.g. $(R^4CO)_2O$) and mixed acid anhydrides (e.g., $R^4COOCOt$-$Bu$ and $R^4COOCOOEt$) of carboxylic acid having $R^4$ ($R^4COOH$). Preferred are acid halides and more preferred is $R^4COCl$.

Examples of Lewis acid include titanium chloride, tin chloride, zinc chloride, zinc bromide, zinc iodide, magnesium chloride, titanium alkoxide, boron bromide, boron chloride, boron fluoride, boron trifluoride-diethyl ether complex, aluminum chloride, aluminum bromide, thionyl chloride, phosphorus oxychloride, phosphorus chloride, trimethylsilyl chloride, trimethylsilyl iodide, trimethylsilyl trifluoromethanesulfonate, and the like. Preferred are thionyl chloride, tin chloride and boron trifluoride-diethyl ether complex, with more preference given to boron trifluoride-diethyl ether complex.

Examples of salts include, but not limited to, alkali metal salts such as sodium salt, potassium salt and cesium salt; alkaline earth metal salts such as calcium salt and magnesium salt; organic amine salts such as triethylamine salt, pyridine salt, picoline salt, ethanolamine salt, triethanolamine salt, dicyclohexylamine salt and N,N'-dibenzylethylenediamine salt; inorganic acid salts such as hydrochloride, hydrobromide, sulfate and phosphate; organic acid salts such as formate, acetate, trifluoroacetate, maleate and tartrate; sulfonates such as methanesulfonate, benzenesulfonate and p-toluenesulfonate; and amino acid salts such as arginine, aspartate and glutamate.

The present invention encompasses various isomers of respective compounds.

The method for producing compound [XV] from (z)-2-butene-1,4-diol which is used as a starting compound, that is, the method for producing compounds inclusive of the above-mentioned final objective compound [XVI] useful as an HIV protease inhibitor is described in detail in the following.

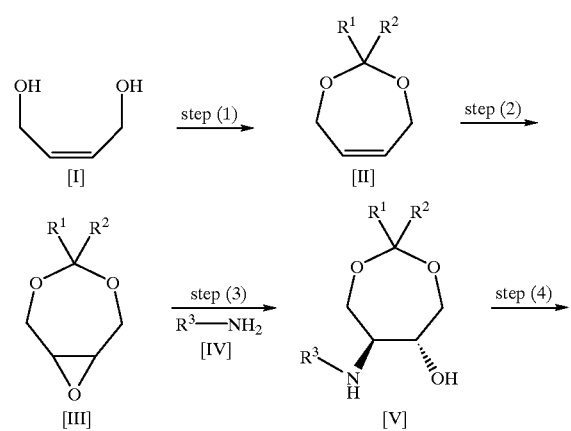

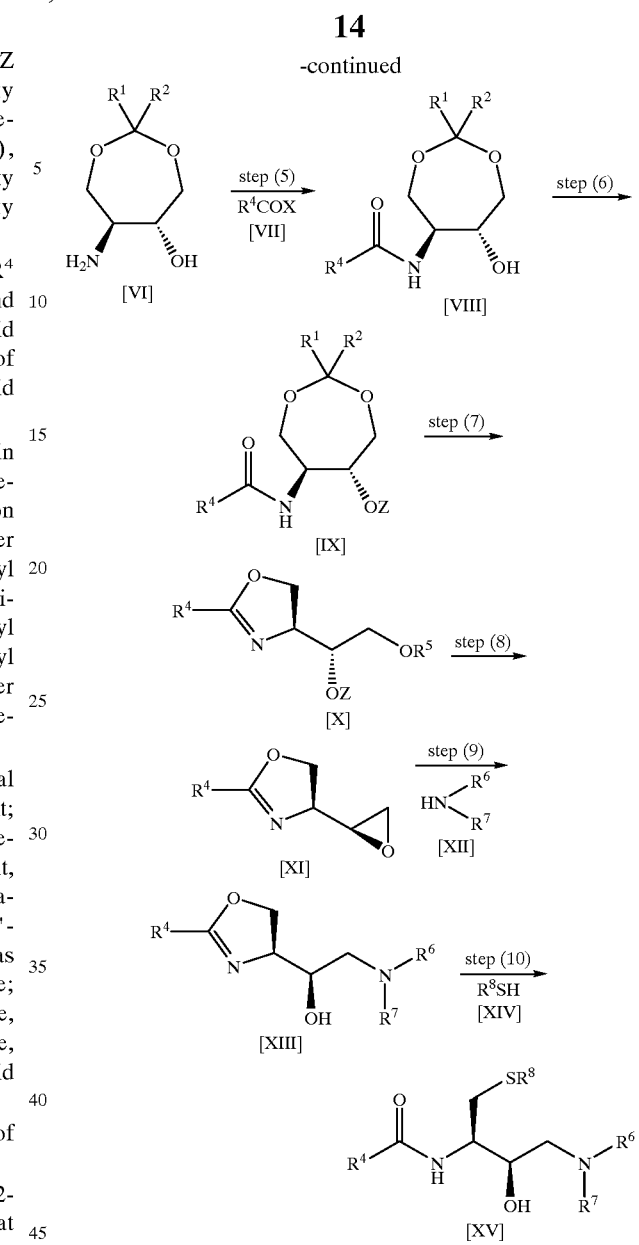

wherein $R^1$, $R^2$, $R^3$, $R^4$, $R^5$, $R^6$, $R^7$, $R^8$ and Z are as defined above, and X is halogen atom, alkoxycarbonyloxy, acyloxy or —$OCOR^4$ wherein $R^4$ is as defined above.

Examples of halogen atom include those mentioned above. Alkoxycarbonyloxy preferably has 2 to 6 carbon atoms and is exemplified by methoxycarbonyloxy, ethoxycarbonyloxy, propoxycarbonyloxy, butoxycarbonyloxy, and the like. Acyloxy preferably has 2 to 6 carbon atoms and is exemplified by acetyloxy, propionyloxy, valeryloxy, pivaloyloxy, and the like.

Step (1): Protection of diol

The reaction per se is known wherein (z)-2-butene-1,4-diol [I] is reacted with an acetalating agent or a ketalating agent without solvent or in a suitable solvent, in the presence of a dehydrating agent or a suitable catalyst such as acid, thereby to protect hydroxyl groups and produce compound [II].

Examples of the acetalating agent and ketalating agent include carbonyl compounds such as formaldehyde, acetaldehyde, benzaldehyde, acetone, diethyl ketone, methyl ethyl ketone, acetophenone, cyclopentanone and cyclohexanone; gem-dialkoxy compounds such as dimethoxymethane, 1,1-dimethoxyacetaldehyde, benzaldehydodimethylacetal, 2,2-dimethoxypropane and cyclohexanone dimethylacetal; vinyl ether compounds such as methyl vinyl ether, ethyl vinyl ether, 2-methoxypropene, 2-ethoxypropene and 1-methoxycyclohexene; and the like. Preferred are gem-dialkoxy compounds with more preference given to 2,2-dimethoxypropane.

The catalyst is appropriately selected according to the kind of acetalating agent and ketalating agent. Suitable catalyst includes, for example, inorganic acids such as sulfuric acid, hydrochloric acid and nitric acid; and organic acids such as acetic acid, trifluoroacetic acid, methanesulfonic acid, p-toluenesulfonic acid, benzenesulfonic acid and camphorsulfonic acid. Preferred are organic acids with more preference given to p-toluenesulfonic acid.

Examples of the dehydrating agent include phosphorus pentoxide, molecular sieves, phosphorus pentachloride, and the like. Preferred are molecular sieves.

The solvent is appropriately selected according to the kind of acetalating agent and ketalating agent. Suitable solvent includes, for example, hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; and polar solvents such as N,N-dimethylformamide, dimethyl sulfoxide, acetonitrile and acetone, with preference given to hydrocarbon solvents and more preference given to a reaction without solvent.

The reaction (refluxing) temperature is suitably 0–200° C., preferably 80–160° C.

The compound [II] can be used directly in the next step without isolation.

Step (2): Epoxidation with oxidizing agent

This step comprises epoxidation of compound [II] without solvent or in a suitable solvent using an oxidizing agent to give compound [III]. Like Step (1), this reaction per se is known (see U.S. Pat. No. 4,439,613).

As the oxidizing agent, inorganic oxidizing agents such as hydrogen peroxide, Oxon (trademark); and organic oxidizing agents such as metachloroperbenzoic acid, peracetic acid and t-butylhydroperoxide can be used. Preferred are inorganic oxidizing agents and more preferred is hydrogen peroxide. In this case, sodium hydroxide, or sodium hydroxide and disodium hydrogenphosphate in combination are desirably co-used for smooth progress of the reaction.

The solvent is appropriately selected according to the kind of oxidizing agent. Suitable solvents include, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, acetonitrile, acetone, formic acid, acetic acid and water; and mixed solvents thereof. Preferred are alcohol solvents and more preferred is a mixed solvent of methanol, acetonitrile and water.

While the reaction temperature varies depending on the oxidizing conditions, it is suitably 0–150° C. and preferably 50–100° C. The reaction time is preferably 3 to 8 hours.

The compound [III] can be used directly in the next step without isolation.

Step (3): Epoxy ring-opening reaction with chiral amine

This step comprises epoxy ring-opening of compound [III] with chiral amine [IV] of the formula: $R^3$—$NH_2$ wherein $R^3$ is as defined above, in a suitable solvent or without solvent, and subjecting the mixture of isomers thus produced to crystallization (e.g. recrystallization) to give an optically pure compound [V] or an enantiomer thereof.

As mentioned above, the chiral amine includes, for example, aralkylamines represented by (R)-1-phenylethylamine, (S)-1-phenylethylamine, (R)-1-(1-naphthyl)ethylamine, (S)-1-(1-naphthyl)ethylamine, (R)-α-phenylglycinol and (S)-α-phenylglycinol; amino acids such as (R)-serine, (S)-serine, (R)-α-phenylglycine and (S)-α-phenylglycine; and amino acid derivatives such as (R)-serine methyl ester, (S)-serine methyl ester, (R)-α-phenylglycine methyl ester and (S)-α-phenylglycine methyl ester, with preference given to chiral aralkylamine and more preference given to chiral 1-phenylethylamine.

By appropriately selecting the chiral amine, a compound [V] or an enantiomer of compound [V] can be obtained.

Suitable solvents to be used for the reaction include, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; polar solvents such as N,N-dimethylformamide, dimethyl sulfoxide, acetonitrile, acetone and water; and mixed solvents thereof. Preferred are alcohol solvents and more preferred is isopropyl alcohol.

The reaction temperature is suitably 0–150° C. and preferably 50–100° C. The reaction time is preferably 20 to 30 hours.

Suitable solvents to be used for crystallization include, for example, alcohol solvents such as methanol, ethanol, n-propyl alcohol, isopropyl alcohol, n-butyl alcohol and t-butyl alcohol; hydrocarbon solvents such as benzene, toluene, hexane, heptane, methylcyclohexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile, acetone and water; and mixed solvents thereof. Preferred are hydrocarbon solvents and a mixed solvent of hydrocarbon solvent and alcohol solvent and more preferred is a mixed solvent of hexane or heptane, and isopropyl alcohol.

Step (4): Removal of chiral element

This step comprises removing chiral element ($R^3$) under suitable conditions from the compound [V] or an enantiomer thereof obtained in Step (3) to give a chiral compound [VI] or an enantiomer thereof.

The conditions of removal are appropriately determined according to the kind of chiral element. For example, when $R^3$ is 1-phenylethyl, the chiral element can be removed by catalytic reduction in a suitable solvent in the presence of a suitable catalyst such as palladium hydroxide, and hydrogen source.

In this case, suitable catalyst includes, for example, palladium catalysts (e.g., palladium hydroxide-carbon, palladium-carbon and palladium-alumina), platinum catalysts (e.g., platinum oxide), rhodium catalysts (e.g., rhodium-alumina) and ruthenium catalysts (e.g., ruthenium-alumina). Preferred are to palladium catalysts with more preference given to palladium hydroxide-carbon.

Examples of the hydrogen source include hydrogen gas, ammonium formate, formic acid, cyclohexadiene, and the like. Preferred is hydrogen gas.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, formic acid, acetic acid and water; and mixed solvents thereof. Preferred are alcohol solvents, polar solvents and a mixed solvent of alcohol solvent and polar solvent, and more preferred is a mixed solvent of isopropyl alcohol, acetic acid and water.

The reaction temperature is suitably 0–100° C. and preferably 20–60° C. The reaction time is preferably 5 to 20 hours.

Step (5): Acylation of amino group

This step comprises acylation of amino group of compound [VI] or an enantiomer thereof using an acylating agent [VII] comprising a reactive carboxylic acid derivative having $R^4$ group, in a suitable solvent in the presence of a suitable base, to give compound [VIII] or an enantiomer thereof.

Examples of $R^4$ of the reactive carboxylic acid derivative having $R^4$ group, which is used as an acylating agent, include optionally substituted alkyl such as methyl, ethyl, propyl, butyl, s-butyl and t-butyl; optionally substituted aryl such as phenyl, 4-tolyl, 3-tolyl, 2-tolyl, 3-acetoxy-2-methylphenyl, 3-hydroxy-2-methylphenyl, 1-naphthyl and 2-naphthyl; optionally substituted heteroaryl such as 2-thienyl, 3-thienyl, 2-furyl, 3-furyl, 2-pyridyl, 3-pyridyl and 4-pyridyl; optionally substituted aralkyl such as benzyl, phenethyl, 1-naphthylmethyl and 2-naphthylmethyl; optionally substituted heteroarylalkyl such as 2-thienylmethyl, 3-thienylmethyl, 2-furylmethyl, 3-furylmethyl, 2-pyridylmethyl, 3-pyridylmethyl and 4-pyridylmethyl; and the like. Preferred are 3-acetoxy-2-methylphenyl and 3-hydroxy-2-methylphenyl.

The reactive carboxylic acid derivative having $R^4$ group is appropriately selected according to the substitution mode of the desired final product, and, for example, acid halides, acid anhydrides and mixed acid anhydrides of carboxylic acid ($R^4COOH$) having $R^4$ group may be used.

Examples of acid halides of carboxylic acid ($R^4COOH$) having $R^4$ group include $R^4COCl$, $R^4COBr$, and the like. Examples of acid anhydride include ($R^4CO)_2O$, and the like. Examples of mixed acid anhydride include $R^4COOCOt$-Bu, $R^4COOCOOEt$, and the like.

Examples of suitable base include organic base such as pyridine, lutidine, picoline, triethylamine, diisopropylethylamine, dimethylaminopyridine, DBU (1,8-diazabicyclo[5.4.0]-7-undecene) and DBN (1,5-diazabicyclo[4.3.0]-5-nonene); and inorganic base such as lithium hydroxide, sodium hydroxide, potassium hydroxide, sodium hydrogencarbonate, potassium hydrogencarbonate, sodium carbonate and potassium carbonate. Preferred are inorganic bases, particularly sodium hydrogencarbonate.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile, acetone and water; and mixed solvents thereof. Preferred is a heterogeneous solvent of Schotten-Baumann comprising halogen solvent and water, and more preferred is a solvent comprising dichloromethane and water.

The reaction temperature is suitably 0–100° C. and preferably 10–40° C. The reaction time is preferably 1 to 5 hours.

The compound [VIII] can be used directly as an extracted solution in the next step without isolation.

Step (6): Sulfonylation of hydroxy

This step comprises introduction of a substituent Z which functions, together with an oxygen atom, as a leaving group wherein the hydroxy of the compound [VIII] or an enantiomer thereof is sulfonylated in a suitable solvent in the presence of a suitable base using a suitable sulfonylating agent to give a compound [IX] or an enantiomer thereof.

Examples of suitable sulfonylating agent include sulfonyl chloride such as methanesulfonyl chloride, benzenesulfonyl chloride, toluenesulfonyl chloride and camphorsulfonyl chloride; sulfonic anhydride such as methanesulfonic anhydride and trifluoromethane-sulfonic anhydride; and the like. Preferred is sulfonyl chloride, and more preferred is methanesulfonyl chloride.

Suitable base includes, for example, organic bases such as pyridine, lutidine, picoline, triethylamine, diisopropylethylamine, dimethylaminopyridine, DBU and DBN. Preferred are pyridine and triethylamine with more preference given to triethylamine.

Suitable solvent includes, for example, hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile and acetone; and mixed solvents thereof. Preferred are halogen solvents and more preferred is dichloromethane.

The reaction temperature is suitably −10–30° C. and preferably 0–20° C. The reaction time is preferably 1 to 10 hours.

The compound [IX] can be used directly as an extracted solution in the next step without isolation.

Step (7): Formation of oxazoline ring

This step comprises treating compound [IX] or an enantiomer thereof with a suitable Lewis acid in a suitable solvent, thereby simultaneously deprotecting 1,3-dioxepane ring and forming oxazoline ring, to give a compound [X] or an enantiomer thereof wherein $R^5$ is hydrogen atom. After the reaction, the obtained compound is treated with a suitable acylating agent in the same reaction vessel to convert hydroxy to acyl to give a stabler compound [X] or an enantiomer thereof wherein $R^5$ is acyl.

Examples of Lewis acid include, as mentioned above, titanium chloride, tin chloride, zinc chloride, zinc bromide, zinc iodide, magnesium chloride, titanium alkoxide, boron bromide, boron chloride, boron fluoride, boron trifluoride-diethyl ether complex, aluminum chloride, aluminum bromide, thionyl chloride, phosphorus oxychloride, phosphorus chloride, trimethylsilyl chloride, trimethylsilyl iodide, trimethylsilyl trifluoromethanesulfonate, and the like. Preferred are thionyl chloride, tin chloride and boron trifluoride-diethyl ether complex. More preferred is boron trifluoride-diethyl ether complex.

Suitable solvent includes, for example, hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile and acetone; and mixed solvents thereof. Preferred are halogen solvents and more preferred is dichloromethane.

Examples of suitable acylating agent include acid halides such as acetyl chloride, benzoyl chloride and pivaloyl chloride; acid anhydrides such as acetic anhydride, benzoic anhydride and pivalic anhydride; and the like. Preferred are acid anhydrides, more preferably acetic anhydride.

The reaction temperature is suitably 0–100° C. and preferably 10–40° C. The reaction time is preferably 1 to 50 hours. The reaction is terminated by adding an aqueous solution of a suitable base. Examples of the suitable base include inorganic bases such as lithium hydroxide, sodium hydroxide, potassium hydroxide, sodium carbonate, potassium carbonate, sodium hydrogencarbonate and potassium hydrogencarbonate; and organic bases such as N,N-dimethylethanolamine and N-methylmorpholine, which are selected as appropriate according to the kind of Lewis acid to be used. For example, when boron trifluoride-diethyl ether complex is used, N-methylmorpholine is preferably used.

The compound [X] can be used directly as a concentration residue in the next step without isolation.

Step (8): Epoxidation

This step comprises treating compound [X] or an enantiomer thereof with a suitable base in a suitable solvent to give compound [XI] or an enantiomer thereof.

Suitable base includes, for example, inorganic bases such as sodium hydride, potassium hydride, lithium hydride, lithium hydroxide, sodium hydroxide, potassium hydroxide, calcium hydroxide, barium hydroxide, sodium carbonate, potassium carbonate, sodium hydrogencarbonate and calcium carbonate; and organic bases such as pyridine, triethylamine, diisopropyl ethylamine, lutidine, DBU, DBN, alkoxides (e.g., sodium methoxide, sodium ethoxide and potassium t-butoxide), and alkali metal amides (e.g., lithium amide, sodium amide, potassium amide and lithium diisopropylamide), with preference given to inorganic bases and more preference given to potassium hydroxide and potassium carbonate.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; polar solvents such as N,N-dimethylformamide, dimethyl sulfoxide, acetonitrile, acetone and water; and mixed solvents thereof. Preferred is a mixed solvent of alcohol solvent and water, and more preferred is a mixed solvent of water and isopropyl alcohol or methanol.

The reaction temperature is suitably 0–100° C. and preferably 0–60° C. The reaction time is preferably 1 to 10 hours.

The compound [XI] can be used as an intermediate in a reaction mixture without isolation, and so-called one-pot reaction can be carried out in the next step.

Step (9): Epoxy ring opening with amine

This step comprises treating compound [XI] or an enantiomer thereof with amine [XII] in a suitable solvent to open epoxy ring, thereby to give a compound [XIII] or an enantiomer thereof.

As the amine, any amine can be used as long as it has at least one hydrogen atom on nitrogen, and examples thereof include ammonia, methylamine, ethylamine, propylamine, isopropylamine, aniline, anisidine, dimethylamine, diethylamine, dipropylamine, diisopropylamine, methylethylamine, methylisopropylamine, methylaniline, pyrrolidine, piperidine, decahydroisoquinoline, (3S, 4aS, 8aS)-decahydroisoquinoline-3-carboxylic acid t-butylamide, and the like.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; polar solvents such as N,N-dimethylformamide, dimethyl sulfoxide, acetonitrile, acetone and water; and mixed solvents thereof. Preferred is a mixed solvent of alcohol solvent and water, and more preferred is a mixed solvent of water and isopropyl alcohol or methanol.

The reaction temperature is suitably 0–100° C. and preferably 20–70° C. The reaction time is preferably 1 to 10 hours.

The compound [XIII] can be obtained all at once by reacting compound [X] which is a starting compound in the previous Step (8), compound [XII] and a suitable base.

Examples of the suitable base include inorganic bases such as sodium hydride, potassium hydride, lithium hydride, lithium hydroxide, sodium hydroxide, potassium hydroxide, calcium hydroxide, barium hydroxide, sodium carbonate, potassium carbonate, sodium hydrogencarbonate and calcium carbonate; and organic bases such as pyridine, triethylamine, diisopropyl ethylamine, lutidine, DBU, DBN, alkoxides (e.g., sodium methoxide, sodium ethoxide and potassium t-butoxide), and alkali metal amides (e.g., lithium amide, sodium amide, potassium amide and lithium diisopropylamide). Preferred are inorganic bases with more preference given to potassium carbonate.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; polar solvents such as N,N-dimethylformamide, dimethyl sulfoxide, acetonitrile, acetone and water; and mixed solvents thereof. Preferred is a mixed solvent of alcohol solvent and water, and more preferred is a mixed solvent of methanol and water.

The reaction temperature is suitably 0–100° C. and preferably 20–70° C.

Step (10): Oxazoline ring opening with thiol

This step comprises reacting compound [XIII] or an enantiomer thereof with thiol [XIV] in a suitable solvent in the presence of a base, thereby simultaneously opening oxazoline ring and thiolating to give a compound [XV] or an enantiomer thereof.

Examples of the thiol include alkylmercaptans such as methylmercaptan, ethylmercaptan, propylmercaptan, isopropylmercaptan, butylmercaptan, s-butylmercaptan and t-butylmercaptan; aralkylmercaptans such as benzylmercaptan; arylmercaptans such as thiophenol and toluenethiol; and the like. Preferred are to arylmercaptans, more preferably thiophenol.

Suitable base includes, for example, inorganic bases such as sodium hydride, potassium hydride, lithium hydride, lithium hydroxide, sodium hydroxide, potassium hydroxide, calcium hydroxide, barium hydroxide, sodium carbonate, potassium carbonate, sodium hydrogencarbonate, potassium hydrogencarbonate and calcium carbonate; and organic bases such as pyridine, triethylamine, diisopropylethylamine, lutidine, DBU, DBN, alkoxides (e.g., sodium methoxide, sodium ethoxide and potassium t-butoxide), and alkali metal amides (e.g., lithium amide, sodium amide, potassium amide and lithium diisopropylamide), with preference given to triethylamine and potassium hydrogencarbonate.

Suitable solvent includes, for example, alcohol solvents such as methanol, ethanol, n-propyl alcohol, isopropyl alcohol, n-butyl alcohol, t-butyl alcohol and ethylene glycol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; polar solvents such as N,N-dimethylformamide, N,N-dimethylacetamide, dimethyl sulfoxide, acetonitrile and acetone; ketone solvents such as methyl isobutyl ketone, diethyl ketone and methyl ethyl ketone; and mixed solvents thereof. Preferred are polar solvents and ketone solvents, and more preferred are N,N-dimethylformamide and methyl isobutyl ketone.

The reaction temperature is suitably 0–150° C. and preferably 80–130° C. The reaction time is preferably 1 to 30 hours.

The enantiomers of the above-mentioned compound [XV] and various intermediates can be obtained by the same reactions as above using an enantiomer of compound [V] obtained in Step (3).

The compound [XV], various intermediates and enantiomers thereof can be obtained at optional purity by appropriately applying separation and purification conventionally known, such as concentration, extraction, chromatography, reprecipitation and recrystallization.

The salts of the above-mentioned compound [XV], various intermediates and various isomers thereof can be produced by a known method.

The present invention is described in detail by way of illustrative Examples in the following, to which the invention is not limited.

Examples are shown in a schematic flow in the following.

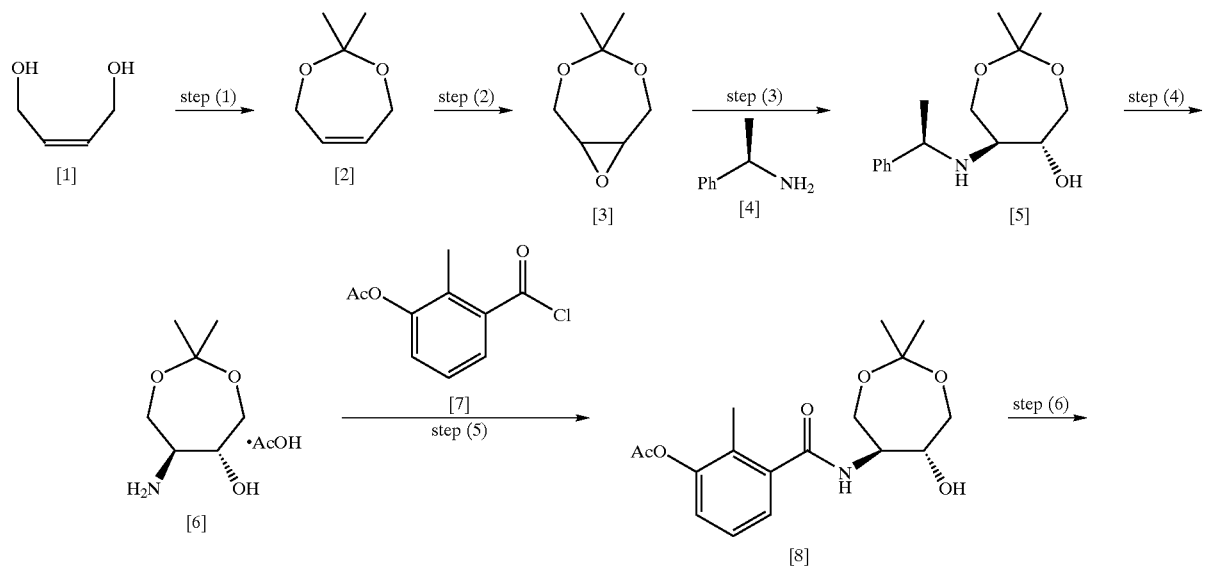

-continued

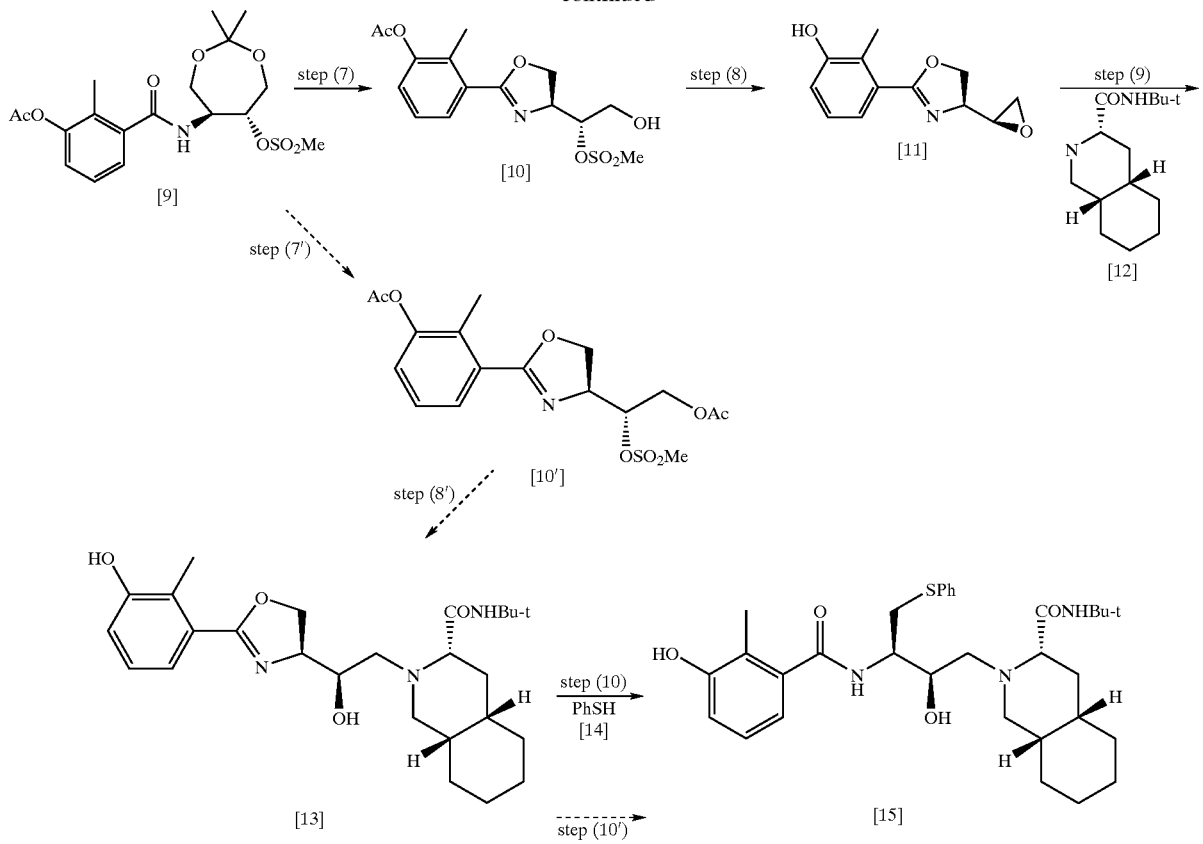

wherein Ph is phenyl, Ac is acetyl, Me is methyl and Bu-t is t-butyl.

REFERENCE EXAMPLE 1

3-Acetoxy-2-methyl Benzoic Acid

3-Nitro-2-methyl benzoic acid (90.5 g, 0.500 mol) was dissolved in 1.0 mol/L aqueous solution (500 ml) of sodium hydroxide. 10% Palladium-carbon (4.5 g) was added and the mixture was stirred under a hydrogen atmosphere (2–3 atm) for 9 hours at 40° C. The catalyst was filtered off and conc. sulfuric acid (94.0 ml) was added under ice-cooling. An aqueous solution of sodium nitrite (35.0 g, 0.500 mol/150 ml) was added over one hour while stirring the mixture at not more than 6° C., and after the dropwise addition, the mixture was heated at 65° C. for 1.5 hours. The inner temperature rose to 57° C. in an hour. The reaction mixture was cooled to room temperature, and saturated brine (300 ml) was added. The mixture was extracted with ethyl acetate (700 ml). The organic layer was washed with saturated brine (200 ml) and dried over magnesium sulfate. The solvent was distilled away to give 3-hydroxy-2-methyl benzoic acid as a pale brown solid.

This substance was dissolved in pyridine (500 ml), and acetic anhydride (100 ml) was added at room temperature, which was followed by stirring at room temperature for 3.5 hours. Ethanol (100 ml) which was kept at not more than 10° C. was added to the reaction mixture, and the mixture was stirred for another hour at room temperature. The mixture was concentrated to give a brown oil. The oil was dissolved in ethyl acetate (800 ml) and washed successively with 1N hydrochloric acid (500 ml) and saturated brine (300 ml). Magnesium sulfate and active charcoal (4.00 g) were added to the organic layer, and the mixture was stirred for 30 minutes. The insoluble matter was filtered off and the filtrate was concentrated to dryness. Acetic acid in this product was removed by azeotropy using toluene (400 ml), and the residue was washed with toluene (450 ml) to give 3-acetoxy-2-methyl benzoic acid (70.1 g, yield 72%) as colorless crystals, melting point 146–148° C. $^1$H-NMR (CDCl$_3$, 300 MHz) δ: 7.95 (dd,1H,J=1.5,7.3 Hz), 7.30 (t,1H, J=7.7 Hz), 7.24 (dd,1H,J=1.5,8.1 Hz), 2.46 (s,3H), 2.36 (s,3H) IR (KBr): 2984, 2816, 1766, 1687, 1460, 1311, 1279, 1211, 1039, 930, 766, 752 cm$^{-1}$ Elemental Analysis ($C_{10}H_{10}O_4$): Calculated: C,61.85;H, 5.19. Found: C,61.91;H,4.94.

EXAMPLE 1

Production of Compound [2] (Step 1)

To a mixture of (z)-2-butene-1,4-diol (compound [1], 211.4 g, 2.4 mol) and 2,2-dimethoxypropane (590.2 ml, 4.8 mol) was added p-toluenesulfonic acid monohydrate (30 mg). The solution thus obtained was evaporated under atmospheric pressure to give a colorless transparent liquid of 2,2-dimethyl-4,7-dihydro-1,3-dioxepine (compound [2], 245 g, yield 80%), boiling point 140–145° C./760 mmHg. $^1$H-NMR (CDCl$_3$, 300 MHz) δ: 5.67 (diffused s,2H), 4.26 (diffused s, 4H), 1.44 (s,6H)

EXAMPLE 2

Production of Compound [3] (Step 2)

2,2-Dimethyl-4,7-dihydro-1,3-dioxepine (compound [2], 94.0 g, 0.734 mol), methanol (220 ml) and acetonitrile (116 ml, 2.20 mol) were mixed and the mixture was heated to 60° C. A 30% aqueous hydrogen peroxide solution (208 ml, 1.84 mol) was dropwise added over 1.5 hours at 60–70° C. Simultaneously, an aqueous solution of 1M sodium hydroxide was dropwise added to adjust the reaction system to a pH of 9.1–9.6. Even after the dropwise addition of the aqueous solution of hydrogen peroxide, the dropwise addition of the aqueous solution of 1M sodium hydroxide was continued, during which time the pH was kept at 9.1–9.6 and temperature at 50–70° C., and the mixture was stirred for 1.5 hours. The reaction mixture was cooled to room temperature, diluted with saturated brine (220 ml) and extracted with chloroform (180 ml×1, 90 ml×2). The organic layers were combined, washed with an aqueous solution of sodium hydrogensulfite (300 ml, 15 g) and dried over magnesium sulfate. The solvent was evaporated and the residue was distilled to give a colorless, transparent liquid of 4,4-dimethyl-3,5,8-trioxabicyclo[5.1.0]octane (compound [3], 86.7 g, yield 82%), boiling point 70–74° C./17 mmHg. $^1$H-NMR (CDCl$_3$, 300 MHz) δ: 4.08–3.97 (m,4H), 3.22–3.18 (m,2H), 1.37 (s,3H), 1.32 (s,3H)

EXAMPLE 3

Production of Compound [5] (Step 3)

4,4-Dimethyl-3,5,8-trioxabicyclo[5.1.0]octane (compound [3], 142 g, 0.988 mol) obtained above and (R)-1-phenylethylamine (compound [4], 120 g, 0.988 mol) were dissolved in isopropyl alcohol (400 ml). The mixture was refluxed under heating for 24 hours and concentrated to 366 g. Hexane (400 ml) was added to the residue and the mixture was stirred at 5° C. for one hour. The precipitated crystals were collected by filtration, washed with hexane and dried to give colorless crystals of (5R, 6S)-2,2-dimethyl-6-[(R)-1-phenylethylamino]-1,3-dioxepan-5-ol (compound [5], 94.0 g, yield 36%), melting point 108–108.5° C.

$^1$H-NMR (CDCl$_3$, 300 MHz) δ: 7.33–7.22 (m,5H), 3.95 (q,1H,J=6.5 Hz), 3.75 (dd,1H,J=1.8,12.1 Hz), 3.74 (dd,1H, J=2.0,12.5 Hz), 3.52 (dd,1H, J=5.5,12.5 Hz), 3.48 (ddd,1H, J=0.5,5.9,12.1 Hz), 3.37 (dt,1H, J=1.4,5.6 Hz), 2.44 (br s,1H), 2.34 (dt,1H,J=1.7,5.5 Hz), 1.34 (d,3H, J=6.5 Hz), 1.34 (s,3H), 1.31 (s,3H)

IR (KBr) 3406, 2590, 1452, 1374, 1219, 1072, 1052, 841, 758, 696 cm$^{-1}$ $[\alpha]_D^{25}$: +91.0° (c1.00, MeOH)

Elemental Analysis (C$_{15}$H$_{23}$NO$_3$): Calculated: C,67.90;H,8.74;N,5.28. Found: C,67.90;H,9.01;N,5.31.

EXAMPLE 4

Production of Compound [6] (Step 4)

20% Palladium hydroxide-carbon (50% wet type, 9.20 g) was suspended in isopropyl alcohol (550 ml), and (5R, 6S)-2,2-dimethyl-6-[(R)-1-phenylethylamino]-1,3-dioxepan-5-ol (compound [5], 92.0 g, 37.7 mmol) and acetic acid (20.8 ml, 37.7 mmol) were added. The mixture was stirred at room temperature under hydrogen atmosphere (3.0 atm) for 8 hours. The catalyst was removed by Celite filtration and the filtrate was concentrated to 105 g. Hexane (400 ml) was added to the residue and the obtained suspension was stirred to allow precipitation of thin crystals. The crystals were collected by filtration and dried to give colorless crystals of (5R, 6S)-6-amino-2,2-dimethyl-1,3-dioxepan-5-ol acetate (compound [6], 76.6 g, yield 100%), melting point 133–134° C. $^1$H-NMR (CDCl$_3$, 300 MHz) δ: 3.84 (dd,1H,J=2.5,12.7 Hz), 3.74 (dd,1H, J=2.5,12.5 Hz), 3.67–3.53 (m,3H), 2.98 (dt,J=2.4,6.5 Hz), 1.91 (s,3H), 1.33 (s,6H)

IR (KBr): 3178, 2993, 1617, 1561, 1525, 1409, 1385, 1223, 1087, 1031, 846 cm$^{-1}$ $[\alpha]_D^{25}$: +29.6° (c1.05, MeOH)

Elemental Analysis (C$_9$H$_{19}$NO$_5$): Calculated: C,48.86;H,8.66;N,6.33. Found: C,48.98;H,8.70;N,6.36.

EXAMPLE 5

Production of Compound [83] (Step 5)

Sodium hydrogencarbonate (42.0 g, 0.500 mol) was suspended in water (350 ml) and (5R, 6S)-6-amino-2,2-dimethyl-1,3-dioxepan-5-ol acetate (compound [6], 44.3 g, 0.200 mol) was added. Then, a solution of 3-acetoxy-2-methylbenzoyl chloride (43.0 g, 0.200 mol) which can be easily obtained from the aforementioned 3-acetoxy-2-methyl benzoic acid by a known method, in ethyl acetate (650 ml) was added at room temperature. The mixture was stirred at room temperature for 12 hours and saturated brine (200 ml) was added. The organic layer was separated, washed with saturated brine (300 ml) and dried over magnesium sulfate. The solvent was distilled away to give a colorless solid of (5R, 6S)-N-(2,2-dimethyl-5-hydroxy-1,3-dioxepan-6-yl)-3-acetoxy-2-methylbenzamide (compound [8], 76.0 g, yield 113%), melting point 93–94° C. $^1$H-NMR (CDCl$_3$, 300 MHz) δ: 7.28–7.22 (m,2H), 7.10 (m,1H), 6.39 (d,1H,J=7.9 Hz), 4.15–4.07 (m,2H), 3.83–3.78 (m,2H), 3.63 (ddd,1H, J=1.5,3.8,12.7 Hz), 3.55 (ddd,1H,J=1.1,3.4,12.7 Hz), 2.98 (br s,1H), 2.34 (s,3H), 2.24 (s,3H), 1.37 (s,3H), 1.33 (s,3H)

IR (KBr): 3305, 2947, 1760, 1638, 1534, 1374, 1218, 1177, 1054, 844 cm$^{-1}$ $[\alpha]_D^{25}$: +35.2° (c1.34, MeOH)

Elemental Analysis (C$_{17}$H$_{23}$NO$_6$): Calculated: C,60.52;H,6.87;N,4.15. Found: C,60.88;H,6.92;N,4.02.

EXAMPLE 6

Production of Compound [9] (Step 6)

(5R, 6S)-N-(2,2-Dimethyl-5-hydroxy-1,3-dioxepan-6-yl)-3-acetoxy-2-methylbenzamide (compound [8], 44.3 g, 0.200 mol) was dissolved in dichloromethane (800 ml), and triethylamine (36.2 ml, 0.260 mol) and methanesulfonyl chloride (18.6 ml, 0.240 mol) were added under ice-cooling. The mixture was stirred for one hour at room temperature. A saturated solution (600 ml) of sodium hydrogencarbonate was added under ice-cooling, and the organic layer was separated, washed successively with a 10% aqueous solution (500 ml) of citric acid and saturated brine (500 ml) and dried over magnesium sulfate. The solvent was distilled away under reduced pressure, and toluene (700 ml) was added to the residue to allow precipitation of crystals. The crystals were collected by filtration under reduced pressure and dried to give colorless crystals of (5R, 6S)-N-(5-methanesulfonyloxy-2,2-dimethyl-1,3-dioxepan-6-yl)-3-acetoxy-2-methylbenzamide (compound [9], 75.9 g, yield 91%), melting point 127–128° C.

$^1$H-NMR (CDCl$_3$, 300 MHz) δ: 7.30–7.25 (m,2H), 7.13 (m,1H), 6.50 (d1H,J=7.3 Hz), 4.65 (m,1H), 4.22–4.18 (m,2H), 3.96 (ddd,1H, J=1.3,3.1,14.1 Hz), 3.88 (dd,1H,J=1.2,14.0 Hz), 3.60 (ddd,1H, J=1.2,3.6,12.9 Hz), 3.24 (s,3H), 2.35 (s,3H), 2.25 (s,3H), 1.39 (s,3H), 1.34 (s,3H)

IR (KBr): 3348, 2941, 1763, 1654, 1639, 1540, 1340, 1207, 1174, 1085, 939, 825 cm$^{-1}$ $[\alpha]_D^{25}$: +73.9° (c1.22, CHCl$_3$)

Elemental Analysis (C$_{18}$H$_{25}$NO$_8$S): Calculated: C,52.04;H,6.07;N,3.37. Found: C,52.20;H,6.12;N,3.42.

EXAMPLE 7

Production of Compound [10] (Step 7)

(5R, 6S)-N-(5-Methanesulfonyloxy-2,2-dimethyl-1,3-dioxepan-6-yl)-3-acetoxy-2-methylbenzamide (compound

[9], 34.2 g, 82.3 mmol) was dissolved in dichloromethane (340 ml) and boron trifluoride-diethyl ether complex (30.4 ml, 247 mmol) was added over 5 minutes with stirring at room temperature. The mixture was stirred for 40 hours at room temperature. Triethylamine (34.5 ml, 247 mmol) was added at not more than 15° C. and the solvent was distilled away under reduced pressure to ⅕ volume. The residue was diluted with ethyl acetate (340 ml) and washed successively with 10% brine (340 ml), 10% brine (340 ml) containing citric acid (17 g), and saturated brine (340 ml). After drying over magnesium sulfate, the solution was concentrated to 36 g to give a crude product of (2R)-2-methanesulfonyloxy-2-((4S)-2-(3-acetoxy-2-methylphenyl)-4,5-dihydrooxazol-4-yl)ethanol (compound [10]).

EXAMPLE 8

Production of Compound [11] (Step 8)

The crude product of compound [10] was suspended in isopropyl alcohol (340 ml) and cooled in an ice bath. An aqueous solution of potassium hydroxide (14.6 g, 260 mmol/68 ml) was added to the suspension at not more than 10° C. and the mixture was stirred at 5° C. for 2.5 hours to give a suspension containing pale yellow (2S)-2-((4S)-2-(3-hydroxy-2-methylphenyl)-4,5-dihydrooxazol-4-yl)oxirane (compound [11]).

EXAMPLE 9

Production of Compound [13] (Step 9)

Acetic acid (14.0 ml, 245 mmol) was added to the mixture obtained in Example 8 at not more than 10° C. to make the mixture acidic, and potassium hydrogencarbonate (25.0 g, 250 mmol) and (3S, 4aS, 8aS)-decahydroisoquinoline-3-carboxylic acid t-butylamide (compound [12], 13.7 g, 57.6 mmol) were successively added. The mixture was stirred at 45° C. for 6 hours to give a pale yellow suspension. The suspension was concentrated to ⅕ and water (340 ml) was added. The suspension was stirred for one hour at room temperature. The resulting crystals were collected by filtration and washed successively with water (200 ml) and butyl acetate (340 ml). The crystals were dried under reduced pressure at 60° C. to give colorless crystals of (3S, 4aS, 8aS)-2-{(2R)-2-[(4S)-2-(3-hydroxy-2-methylphenyl)-4,5-dihydrooxazol-4-yl]-2-hydroxyethyl}decahydroisoquinoline-3-carboxylic acid t-butylamide (compound [13], 17.3 g, yield 46%, from compound [9]), melting point 240° C. $^1$H-NMR (D$_6$-DMSO, 300 MHz) δ: 9.48 (br.s,1H), 7.36 (s,1H), 7.08 (dd,1H,J=1.5, 7.7 Hz), 7.02 (t,1H,J=7.7 Hz), 6.89 (dd,1H,J=1.4,7.7 Hz), 4.74 (d,1H,J=5.4 Hz), 4.46 (m,1H), 4.28 (dd,1H,J=8.1,9.9 Hz), 4.15 (t,1H,J=8.1 Hz), 3.75 (m,1H), 2.91 (br.d,1H,J= 10.3 Hz), 2.58 (dd,1H, J=2.6,11.0 Hz), 2.36 (dd,1H,J=8.8, 12.8 Hz), 2.28 (s,3H), 2.12–2.03 (m,2H), 1.99–1.81 (m,2H), 1.60–1.54 (m,2H), 1.56–1.48 (m,3H), 1.32–1.19 (m,5H), 1.24 (s,9H)

IR (KBr): 3238, 2928, 1645, 1624, 1578, 1560, 1460, 1362, 1279, 1128, 1048 cm$^{-1}$ $[α]_D^{25}$ : 47.3° (c1.02, DMF)

Elemental Analysis (C$_{26}$H$_{39}$N$_3$O$_4$): Calculated: C,68.24;H,8.59;N,9.18. Found: C,68.30;H,8.83;N,9.06.

EXAMPLE 10

Production of Compound [15] (Step 10)

(3S, 4aS, 8aS)-2-{(2R)-2-[(4S)-2-(3-Hydroxy-2-methylphenyl)-4,5-dihydrooxazol-4-yl]-2-hydroxyethyl}decahydroisoquinoline-3-carboxylic acid t-butylamide (compound [13], 16.9 g, 37.0 mmol) was suspended in pyridine (170 ml) and thiophenol (15.2 ml, 148 mmol) was added at room temperature. The mixture was stirred at 80° C. for 13 hours. The mixture was cooled to room temperature and active charcoal (1.70 g) was added. The mixture was stirred at room temperature for 30 minutes and unnecessary matter was removed using Celite. The filtrate was concentrated and the residual pyridine was removed by azeotropy with 2-butanone (150 ml). 2-Butanone (200 ml) was added to the residue and the mixture was refluxed for 2 hours with stirring, during which procedure colorless crystals precipitated. The mixture was left standing at −15° C. for 40 hours and the resulting crystals were collected by filtration. The crystals were washed with a 2-butanol:toluene (1:1) solution (150 ml) and dried in vacuo at 50° C. to give colorless crystals of (3S, 4aS, 8aS)-2-[(2R, 3R)-2-hydroxy-3-(3-hydroxy-2-methylbenzoylamino)-4-phenylthiobutyl]decahydroisoquinoline-3-carboxylic acid t-butylamide (compound [15], 14.4 g, yield 69%).

EXAMPLE 11

Production of Compound [10'] (Step 7')

(5R, 6S)-N-(5-Methanesulfonyloxy-2,2-dimethyl-1,3-dioxepan-6-yl)-3-acetoxy-2-methylbenzamide (compound [9], 786 g, 1.89 mol) was dissolved in dichloromethane (6.29 L), and boron trifluoride diethyl ether (698 ml, 5.68 mol) was added, which was followed by stirring at room temperature for 23 hours. The reaction mixture was cooled to 11° C. and acetic anhydride (268 ml, 2.84 mol) was added, which was followed by stirring at said temperature for 2 hours. The reaction mixture was concentrated to 2.0 kg under reduced pressure and toluene (3.8 L) was added to the obtained residue to give a suspension. N,N-Dimethylethanolamine (571 ml, 5.68 mol) was added to the suspension over 40 minutes at not more than 20° C. Toluene (1.5 L) and water (4.8 L) were added and the mixture was stirred for one hour at room temperature. The organic layer was separated, washed successively with a 10% aqueous citric acid solution (5.00 L) and a 2% aqueous potassium carbonate solution (5.00 L) and dried over magnesium sulfate. The desiccant was filtered off and the filtrate was concentrated under reduced pressure to give (2R)-1-acetoxy-2-((4S)-2-(3-acetoxy-2-methylphenyl)-4,5-dihydrooxazol-4-yl)-2-methanesulfonyloxyethane (compound [10'], 1.04 kg) as a dark red oil. $^1$H-NMR (CDCl$_3$, 300 MHz) δ: 7.68 (d,1H,J=7.7 Hz), 7.26 (t,1H,J= 7.9 Hz), 7.14 (d,1H,J=8.0 Hz), 5.02 (dt,1H,J=7.7,3.7 Hz), 4.66 (ddd,1H, J=3.6,8.1,9.5 Hz), 4.53 (dd,1H,J=3.3,12.4 Hz), 4.47–4.38 (m,3H), 3.11 (s,3H), 2.40 (s,3H), 2.34 (s,3H), 2.10 (2,3H)

EXAMPLE 12

Production of Compound [13] (Step 8')

The unpurified (2R)-1-acetoxy-2-((4S)-2-(3-acetoxy-2-methylphenyl)-4,5-dihydrooxazol-4-yl)-2-methanesulfonyloxyethane (compound [10'], 1.04 kg, 1.89 mol) obtained in Example 11 was suspended in isopropyl alcohol (4.8 L) and an aqueous potassium hydroxide solution (531 g/1.6 L, 9.46 mol) was dropwise added over 45 minutes at not more than 18° C., which was followed by stirring for one hour at 10° C. Acetic acid (325 ml, 5.68 mol) was added at not more than 10° C. to neutralize the mixture, and potassium hydrogencarbonate (568 g, 5.68 mol) and (3S, 4aS, 8aS)-decahydroisoquinoline-3-carboxylic acid t-butylamide (compound [12], 361 g, 1.51 mol) were successively added. The mixture was stirred at 40° C. for 6 hours and the resulting crystals were collected by filtration. The crystals were suspended in water (5.5 L) and the suspension was stirred for 30 minutes. The crystals were again collected by filtration, washed with water (2.5 L) and butyl acetate (4.00 L), and dried under reduced pressure at 60° C. to give (3S, 4aS, 8aS)-2-{(2R)-2-[(4S)-2-(3-hydroxy-2-methylphenyl)-4,5-dihydrooxazol-4-yl]-2-hydroxyethyl}decahydroisoquinoline-3-carboxylic acid t-butylamide (compound [13], 443 g, yield 51%, from compound [9]) as colorless crystals.

EXAMPLE 13

Production of Compound [15] (Step 10')

(3S, 4aS, 8aS)-2-{(2R)-2-[(4S)-2-(3-Hydroxy-2-methylphenyl)-4,5-dihydrooxazol-4-yl]-2-hydroxyethyl}decahydroisoquinoline-3-carboxylic acid t-butylamide (compound [13], 410.5 g, 0.897 mol) was suspended in N,N-dimethylformamide (2.47 L), and triethylamine (1.00 L, 7.18 mol) and thiophenol (368 ml, 3.59 mol) were added, which was followed by stirring at 75° C. for 10 hours. The mixture was cooled to room temperature and the reaction mixture was dropwise added into water (7.5 L) over 30 minutes. The resulting crystals were collected by filtration and resuspended in toluene (7.00 L), which was followed by stirring for 30 minutes. The crystals were again collected by filtration and dried at 60° C. for 34 hours under reduced pressure. The crude crystals were suspended in methyl ethyl ketone (10.0 L) and refluxed under heating to give a solution, which was left standing at room temperature for 16 hours to allow recrystallization. The crystals were collected by filtration, washed with methyl ethyl ketone (1.00 L) and dried at 60° C. for 6 hours under reduced pressure to give (3S, 4aS, 8aS)-2-[(2R, 3R)-2-hydroxy-3-(3-hydroxy-2-methylbenzoylamino)-4-phenylthiobutyl]decahydroisoquinoline-3-carboxylic acid t-butylamide (compound [15], 330.1 g, yield 65%) as colorless crystals.

EXAMPLE 14

Production of Compound [13] (Step 8')

The crude product of (2R)-1-acetoxy-2-((4S)-2-(3-acetoxy-2-methylphenyl)-4,5-dihydrooxazol-4-yl)-2-methanesulfonyloxyethane (compound [10'], 1.98 kg, 3.30 mol) obtained in Example 11 was suspended in a mixed solvent of methanol (6.50 L) and water (6.50 L), and (3S, 4aS, 8aS)-decahydroisoquinoline-3-carboxylic acid t-butylamide (compound [12], 642 g, 2.62 mol) and potassium carbonate (1.36 kg, 9.81 mol) were successively added, which was followed by stirring at 50° C. for 5.5 hours. Water (6.50 L) was added to cool the reaction mixture to room temperature and the resulting crystals were collected by filtration. These crude crystals were again suspended in water (6.50 L), stirred, washed and collected by filtration. The obtained crystals were re-suspended in methyl isobutyl ketone (10.0 L) and the suspension was subjected to azeotropic dehydration. The obtained residue was cooled to room temperature and crystals were collected by filtration to give (3S, 4aS, 8aS)-2-{(2R)-2-[(4S)-2-(3-hydroxy-2-methylphenyl)-4,5-dihydrooxazol-4-yl]-2-hydroxyethyl}decahydroisoquinoline-3-carboxylic acid t-butylamide (compound [13], 902 g, 1.97 mol, yield 60%, from compound [6]) as colorless crystals.

EXAMPLE 15

Production of Compound [15] (Step 10')

(3S, 4aS, 8aS)-2-{(2R)-2-[(4S)-2-(3-Hydroxy-2-methylphenyl)-4,5-dihydrooxazol-4-yl]-2-hydroxyethyl}decahydroisoquinoline-3-carboxylic acid t-butylamide (compound [13], 701 g, 1.53 mol) was suspended in methyl isobutyl ketone (7.00 L), and thiophenol (314 ml, 3.06 mol) and potassium hydrogencarbonate (76.6 g, 0.765 mol) were added. The mixture was refluxed under heating for 12 hours under a nitrogen stream. After the completion of the reaction, toluene (7.00 L) was added, and the precipitated crystals were collected by filtration and washed with toluene. These crude crystals were washed with heating in a mixed solvent of acetone and water (1:1) to give (3S, 4aS, 8aS)-2-[(2R, 3R)-2-hydroxy-3-(3-hydroxy-2-methylbenzoylamino)-4-phenylthiobutyl]decahydroisoquinoline-3-carboxylic acid t-butylamide (compound [15], 695 g, 1.22 mol, yield 80%) as colorless crystals.

The production method of the present invention is extremely easy and simple as compared to the conventional methods, and enables effective production of compound [XV] at high yields, which includes compound [XVI] having an HIV protease inhibitory action. In addition, the novel intermediates of the present invention are extremely useful as intermediates for producing not only the aforementioned compound [XVI] but also compounds useful as X-ray contrast media such as the compounds for X-ray image development as described in U.S. Pat. No. 4,439,613.

What is claimed is:

1. A 4-(2-amino-1-hydroxyethyl)oxazoline derivative of the formula [XIII]

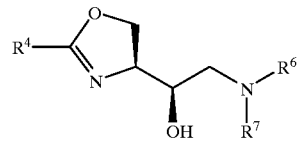

[XIII]

wherein $R^4$ is an optionally substituted alkyl, an optionally substituted aryl, an optionally substituted heteroaryl, an optionally substituted aralkyl or an optionally substituted heteroarylalkyl, and $R^6$ and $R^7$ are the same or different and each is a hydrogen atom, an optionally substituted alkyl, an optionally substituted aryl, an optionally substituted heteroaryl or an optionally substituted aralkyl, or $R^6$ and $R^7$ combinedly form, together with the adjacent nitrogen atom, a hetero ring, said hetero ring being optionally substituted by halogen atom, alkyl, alkenyl, alkoxy, amino, alkoxycarbonyl, carboxamide or alkyl-substituted carbamoyl, an enantiomer thereof or a salt thereof.

2. A method for producing a 4-(2-amino-1-hydroxyethyl)oxazoline derivative of the formula [XIII]

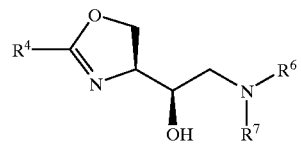

[XIII]

wherein $R^4$ is an optionally substituted alkyl, an optionally substituted aryl, an optionally substituted heteroaryl, an optionally substituted aralkyl or an optionally substituted heteroarylalkyl, and $R^6$ and $R^7$ are the same or different and each is a hydrogen atom, an optionally substituted alkyl, an optionally substituted aryl, an optionally substituted heteroaryl or an optionally substituted aralkyl, or $R^6$ and $R^7$ combinedly form, together with the adjacent nitrogen atom, a hetero ring, said hetero ring being optionally substituted by halogen atom, alkyl, alkenyl, alkoxy, amino, alkoxycarbonyl, carboxamide or alkyl-substituted carbamoyl, or an enantiomer thereof, comprising reacting an (oxazolin-4-yl)oxyrane derivative of the formula [XI]

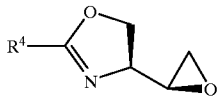
[XI]

wherein $R^4$ is as defined above, or an enantiomer thereof, with an amine of the formula [XII]

[XII]

wherein $R^6$ and $R^7$ are as defined above.

3. A method for producing a 4-(2-amino-1-hydroxyethyl) oxazoline derivative of the formula [XIII]

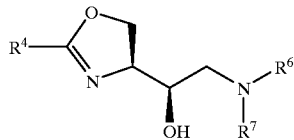
[XIII]

wherein $R^4$ is an optionally substituted alkyl, an optionally substituted aryl, an optionally substituted heteroaryl, an optionally substituted aralkyl or an optionally substituted heteroarylalkyl, and $R^6$ and $R^7$ are the same or different and each is a hydrogen atom, an optionally substituted alkyl, an optionally substituted aryl, an optionally substituted heteroaryl or an optionally substituted aralkyl, or $R^6$ and $R^7$ combinedly form, together with the adjacent nitrogen atom, a hetero ring, said hetero ring being optionally substituted by halogen atom, alkyl, alkenyl, alkoxy, amino, alkoxycarbonyl, carboxamide or alkyl-substituted carbamoyl, or an enantiomer thereof, comprising treating an oxazoline derivative of the formula [X]

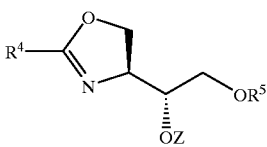
[X]

wherein $R^4$ is as defined above, $R^5$ is a hydrogen atom or an acyl, and Z is a substituent which functions as a leaving group together with an oxygen atom, or an enantiomer thereof with a base to give an (oxazolin-4-yl)oxyrane derivative of the formula [XI]

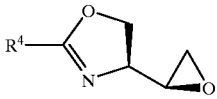
[XI]

wherein $R^4$ is as defined above, or an enantiomer thereof, and reacting the resulting derivative [XI] with an amine of the formula [XII]

[XII]

wherein $R^6$ and $R^7$ are as defined above.

* * * * *